(12) United States Patent
Zilbershlag et al.

(10) Patent No.: US 8,075,472 B2
(45) Date of Patent: Dec. 13, 2011

(54) PERMANENT VENTRICULAR ASSIST DEVICE FOR TREATING HEART FAILURE

(75) Inventors: Michael Zilbershlag, Givat Shmuel (IL); Moshe Levy, Tel Mond (IL)

(73) Assignee: Leviticus-Cardio Ltd., Givat Shmuel (IL)

( * ) Notice: Subject to any disclaimer, the term of this patent is extended or adjusted under 35 U.S.C. 154(b) by 49 days.

(21) Appl. No.: 12/527,595

(22) PCT Filed: May 4, 2008

(86) PCT No.: PCT/IL2008/000604
§ 371 (c)(1),
(2), (4) Date: Aug. 18, 2009

(87) PCT Pub. No.: WO2008/135988
PCT Pub. Date: Nov. 13, 2008

(65) Prior Publication Data
US 2010/0076247 A1    Mar. 25, 2010

Related U.S. Application Data

(60) Provisional application No. 60/915,693, filed on May 3, 2007.

(51) Int. Cl.
*A61N 1/00* (2006.01)
(52) U.S. Cl. .......................................................... 600/17
(58) Field of Classification Search ..................... 600/16, 600/17
See application file for complete search history.

(56) References Cited

U.S. PATENT DOCUMENTS

| 5,507,629 A | 4/1996 | Jarkiv |
| 6,129,704 A | 10/2000 | Forman |
| 6,135,729 A | 10/2000 | Aber |
| 2003/0163020 A1* | 8/2003 | Frazier ........................... 600/16 |

FOREIGN PATENT DOCUMENTS

WO    WO2007003351    1/2007

OTHER PUBLICATIONS

WIPO, "Written Opinion of the International Search Authority for PCT/IL2008/000604," Jan. 31, 2009, European Patent Office, Netherlands.

* cited by examiner

*Primary Examiner* — George Manuel
*Assistant Examiner* — Robert Wieland (57) ABSTRACT

The invention is a kit for a permanent ventricular assist device that can be permanently implanted into the circulatory system of a patient. The kit comprises one or more passive cores (Pcore), a stator, a power supply, and a controller unit. The inventors have realized that major open heart surgery, generally used for implementing a magnetic blood pump in the circulatory system, can be wholly avoided if the rotor and the stator are physically separated and are implanted respectively inside and around the blood vessel at the location of interest. Therefore the kit is characterized in that the one or more Pcores are configured to allow them to be implanted inside a blood vessel and the stator is configure to enable it to be placed outside of the blood vessel surrounding the Pcores. Also described are illustrative medical procedures for implanting the components of the kit at different locations in the body.

4 Claims, 5 Drawing Sheets

PERMANENT VENTRICULAR ASSIST DEVICE FOR TREATING HEART FAILURE

CROSS-REFERENCE TO RELATED APPLICATIONS

This patent application is a National Stage application filed under 35 U.S.C. § 371 of PCT/IL2008/000604 filed on May 4, 2008 and published as WO/2008/135988, which claims priority to US Provisional Patent Application No. 60/915,693 filed on May 3, 2007 which are both hereby incorporated in their entirety by reference.

FIELD OF THE INVENTION

The present invention relates generally to a ventricular assist device for treating congestive cardiac failure, and more particularly to a device that can be permanently implanted into the circulatory system of a patient.

BACKGROUND OF THE INVENTION

Congestive heart failure (CHF), also called congestive cardiac failure (CCF) or just heart failure, is the pathophysiologic state in which the heart, via an abnormality of cardiac function, fails to pump blood at a rate commensurate with the requirements of the metabolizing tissues. Heart failure may be caused by cardiomyopathy, heart valves damage, coronary heart disease, hypertension or in some cases diabetes. The heart compensates for the pumping insufficiency by dilating the ventricular chambers, thickening the walls (hypertrophy), and accelerating the pulsation rates.

More than 11 million patients currently suffer from CHF worldwide with a annual increase of about 10% of cases. Approximately 1 million patients present severe CHF conditions, and 1% are admitted in terminal condition. Nowadays, CHF is considered as the fastest-growing clinical cardiac disease entity in the United States, affecting 2% of the population. Nearly 1 million hospital admissions for acute decompensated CHF occur in the United States yearly, almost double the number seen 15 years ago. The rehospitalization rates during the 6 months following discharge are as high as 50%. Nearly 2% of all hospital admissions in the United States are for decompensated CHF, and heart failure is the most frequent cause of hospitalization in patients older than 65 years. The average duration of hospitalization is about 6 days. An estimated $23 billion are spent on inpatient management of CHF every year, and another $40 billion are spent in the outpatient setting on patients with compensated or mildly decompensated heart failure every year. Despite aggressive therapies, hospital admissions for CHF continue to increase, reflecting the prevalence of this malady.

Heart transplants have been the gold standard of treatment for end-stage CHF. A heart transplant is the replacement of a diseased heart with a healthy one from an organ donor. Candidates for transplant have irreparably damaged hearts, are facing imminent death, and have otherwise viable vital organs. Transplanted hearts generally fail 9.5 years (on average) after implantation. The American National Heart, Lung, and Blood Institute estimated that as many as 100,000 Americans would benefit from a transplant each year. Of these, fewer than 8,000 are ever placed on the national transplant waiting list, and only 2,000 to 2,500 hearts become available for transplantation. Most patients spend months or years waiting for a suitable donor heart and die before one becomes available. As of December 2006, 40,363 heart transplants have been performed in the United States. Nearly 85% of transplant recipients survive over one year following the procedure, and 70% survive for over 5 years. Over 3,000 transplants are performed worldwide each year, including 2,125 in the U.S. in 2005.

A ventricular assist device (VAD), is an electro-mechanical device that is used to partially or completely replace the function of a failing heart. Some VADs are intended for short term use, typically for patients recovering from heart attacks or heart surgery, while others are intended for long term use (months to years and in some cases for life), typically for patients suffering from CHF. VADs need to be clearly distinguished from artificial hearts, which are designed to completely take over cardiac function and generally require the removal of the patient's heart. VADs are designed to assist either the right (RVAD) or left (LVAD) ventricle. The choice of device depends on the underlying heart disease and the pulmonary arterial resistance which determines the load on the right ventricle. LVADs are most commonly used but when pulmonary arterial resistance is high, right ventricular assist becomes necessary. Long term VADs are normally used to keep patients alive with a good quality of life while they wait for a heart transplant.

Most VADs operate on similar principles. A cannula is inserted into the apex of the appropriate ventricle. Blood passes through this to a pump and thence through a tube to the aorta in the case of an LVAD or to the pulmonary artery in the case of an RVAD. The pump is powered through a lead which connects it to a controller and power supply. The first generation VADs, like the one described in U.S. Pat. No. 4,906,229, emulate the heart by using a pulsatile action where blood is alternately sucked into the pump from the left ventricle then forced out into the aorta. These devices are usually cumbersome and necessitate major surgery for their implantation into the vascular system and for introducing the cannula into the heart ventricule. More recent devices are based on intravascular continuous flow pumps, which can be roughly categorized as either centrifugal pumps, like in US 2004/0143151, or axial flow impeller driven pumps, like in U.S. Pat. No. 4,957,504. These second generation VADs have impellers with high flow rate capability and are much smaller than the first generation VADs, but have contacting bearings that suspend the rigid motor. The bearing contacts generally cause undesirable clot formation either inside or around the periphery of the bearings, making these devices unsuitable for long-term use. In these pumps, blood experiences traumatisation and damage due to shearing and vortexing into the small gaps between the outer edge of the stator blades and the inner side of the pipe carrying blood. Latest generation VADs overcome these issues by suspending the impeller in the pump using either hydrodynamic or electromagnetic suspension. therefore decreasing risks of thrombosis or hemolysis. Such pumps are described for example in U.S. Pat. No. 6,527,699 or US 2004/0115038.

The blood can be conveyed to the pump by an external tubular system, like in U.S. Pat. No. 6,742,999, and accelerated therein, but most of the blood pumps are implanted directly into the vascular system. Implantation of a blood pump inside the vascular system is disclosed for example in U.S. Pat. No. 7,144,364. A blood pump is attached to the interior of a stent and inserted into a peripheral artery by catheterisation and advanced to a position at a region of interest. The stent and attached pump are released from the catheter and the pump is activated to increase blood flow. However, implantability of current blood pumps is limited by their inherent characteristics. Latest generation blood pump are implanted in large vessels, as the whole device that comprises both rotor and stator, unavoidably occupies a large volume in the circulatory system. Furthermore, blood pumps have to be wired to a power supply and a controlling unit in order to generate a homogenous rotating electromagnetic field that activates the stator. Therefore perforation of the vascular system near the implantation site is required to allow passage of the wires.

It is an object to this invention to provide a permanent ventricular assist device (PVAD) that can allow a patient suffering from congestive heart failure to live a normal life.

It is further an object to this invention to provide a PVAD which overcome the disadvantages of prior art devices.

It is still another object to the present invention to provide a method to implant the PVAD of the invention in a region of interest.

Other objects and advantages of present invention will appear as description proceeds.

SUMMARY OF THE INVENTION

In a first aspect the invention is a kit for a permanent ventricular assist device (PVAD). The kit comprises one or more passive cores (Pcore), a stator, a power supply, and a controller unit. The kit is characterized in that the one or more Pcores are configured to allow them to be implanted inside a blood vessel and the stator is configure to enable it to be placed to outside of the blood vessel surrounding the Pcores.

The Pcore comprises a cylindrically shaped hollow body, a rotor, comprising a cylinder with an Archimedes screw on its outer surface and magnetic bearings, wherein the rotor is suspended coaxially within the hollow body by means of the magnetic bearings.

In embodiments of the invention the kit may comprise a chassis to which the one or more Pcores are attached by means of either a permanent or a releasable connection.

The rotor of the Pcore a either made of a permanently magnetized material or comprises permanent magnets embedded within it.

The stator is a flexible belt or a bracelet, which comprises at least two independent sets of electromagnets. In preferred embodiments of the invention, the electromagnets are planar elongated bifilar coils. Each set of electromagnets has its own power supply and controller and each electromagnet in a set is electrically connected separately to the power supply and the controller.

The kit of the invention is used for treating heart failure in a patient. Preferably the number of Pcores is selected according to the physiological condition of the patient.

In a second aspect the invention is a medical procedure for implanting components of a kit according to the first aspect.

For example, a procedure for installing the components of the kit according to the first aspect of the invention in the abdominal aorta, by open surgery, comprises the steps of:
  i) Supine position; Trans-Eosophagial ECHO; CVP/Swan-Ganz catheter;
  ii) Exposing the abdominal aorta by midline laparotomy;
  iii) Introducing Systemic Heparin at a ratio of 1 mg/kg;
  iv) Clamping of the Aorta below the renal arteries and above the iliac arteries;
  v) Performing a 3 cm longitudinal cut in the aorta;
  vi) Inserting the Pcore and securing it to the aortic wall;
  vii) Suturing the aorta;
  viii) Placing the stator around the aorta;
  ix) Pulling out the electric command cable through the skin;
  x) Turning the PVAD on, gradually increasing the pump flow; and
  xi) Closing the skin.

In another example, a procedure for installing the components of the kit according to the first aspect of the invention in the lower-abdominal, renal-abdominal or descending thoracic aorta, by catheterization comprises the steps of:
  i) Positioning Supine; Trans-Eosophagial ECHO; CVP/Swan-Ganz catheter;
  ii) Opening the right groin;
  iii) Exposing the right femoral artery;
  iv) Introducing Systemic Heparin at a ratio of 1 mg/kg;
  v) Inserting a "working cuff" into the artery;
  vi) Inserting a J-Wire through the cuff;
  vii) Locating the wire under roentgen guidance to one of three possible locations:
    a) In the lower abdominal aorta;
    b) In the abdominal aorta, above the renal arteries just below the diaphragm;
    c) In the descending thoracic aorta;
  viii) Inserting the stent on the wire to its place;
  ix) Deploying the stent;
  x) Inserting the Pcore on the wire into the stent;
  xi) Anchoring the Pcore to the stent wall;
followed by the introduction of the stator by laparoscopy, as follows:
  xii) Positioning Trendelenburg;
  xiii) For the abdominal locations:
    a) Inserting a videoscopic trocar through the umbilicus;
    b) Inserting two working arms into the abdomen;
    c) Exposing the aorta through the retro-peritoneum;
  xiv) For the thoracic location:
    a) Collapse of the left lung (right lung ventilation);
    b) Inserting a videoscopic trocar lateral to the nipple;
    c) Inserting two working arms into the left thorax;
    d) Exposing the aorta;
  xv) Placing the stator around the Aorta; Roentgen guided position;
  xvi) Pulling out the electric command cable through the skin;
  xvii) Turning the VAD on, gradually increasing the pump flow;
  xviii) Closing the skin;
  xix) Pulling out the femoral cuff;
  xx) Suturing the arteriotomy; and
  xxi) Closing the skin of the groin.

Another example is a procedure for installing the components of the kit according to the first aspect of the invention in the ascending thoracic aorta comprises the steps:
  i) Positioning Supine. Trans-Eosophagial ECHO. CVP/Swan-Ganz catheter;
  ii) Opening the right groin;
  iii) Exposing the right femoral artery;
  iv) Introducing Systemic Heparin at a ratio of 1 mg/kg;
  v) Inserting a "working cuff" into the artery;
  vi) Inserting a J-Wire through the cuff;
  vii) Locating the wire under roentgen guidance in the ascending aorta;
  viii) Inserting the stent on the wire to its place;
  ix) Deploying the stent;
  x) Inserting the Pcore on the wire into the stent;
  xi) Anchoring the Pcore to the stent wall;
followed by the introduction of the stator by thoracoscopy, as follows:
  xii) Ventilating left lung ventilation (Collapse right);
  xiii) Inserting a videoscopic trocar through the right $4^{th}$ intercostals space;
  xiv) Inserting two working arms into the right thorax;
  xv) Exposing the ascending aorta through the pericard;
  xvi) Placing the stator around the aorta;

xvii) Positioning guided by Roentgen.

xviii) Pulling out the electric command cable through the skin.

xix) Turning the VAD on, gradually increasing the pump flow;

xx) Closing the skin;

xxi) Pulling out the femoral cuff;

xxii) Suturing the arteriotomy; and xxiii) Closing sub-cutane and skin of the groin.

In a third aspect the invention is a ranging procedure performed during the phase of installing a PVAD in order to adapt the PVAD of a kit according to the first aspect of the invention to specific installation parameters. The procedure comprises the steps:

i) using the controller to activate the coils in default configuration;

ii) opening a ranging window;

iii) closing the ranging window;

iv) determining the number of coils according to the number of returning signals;

v) determining the position of the coils according to the phase delay of each returning signal from each coil exist;

vi) determining the number of Pcores that are present;

vii) determining the voltage level required from the controller to to maintain the correct RPM of the rotors; and viii) generating an appropriate signal sequence, sending an electrical signal to each coils with the correct phase and voltage.

The ranging procedure may further comprising a step of calibrating the pulse phase to the heart beat by sending pulses from the controller to the pump, in different phase relative to the ECG and measuring the effect on the pump flow.

In a fourth aspect, the invention is a method to adapt in real-time the amount of assistance provided to the heart by the PVAD of the kit of the first aspect of the invention. The method comprises the steps of providing sensors to continuously monitor the ECG to determine the heart rate and beat phase and sending the output of the sensors to the controller, which adjusts the voltage to the coils of the stator and the phase shift in accordance with the modified cardiac cycle, thereby changing the output of the pump accordingly.

BRIEF DESCRIPTION OF THE DRAWINGS

The above and other characteristics and advantages of the invention will be more readily apparent through the following examples, and with reference to the appended drawings, wherein.

DETAILED DESCRIPTION OF THE INVENTION

The present invention is a permanent ventricular assist device (PVAD) used for treating congestive heart failure; thereby enabling a patient in need to lead a normal life. The invention achieves this goal by means of a magnetic blood pump which has its blood conveying part, or rotor, physically separated from the stator by the wall of the blood vessel in which it is implanted. The inventors have realized that major open heart surgery, generally used for implementing a magnetic blood pump in the circulatory system, can be wholly avoided if the rotor and the stator are physically separated and are implanted respectively inside and around the blood vessel at the location of interest. Despite the physical separation of the two major elements of the blood pump, the PVAD of the invention is fully functional and can be permanently implanted in the body of the patient without the necessity of cutting or puncturing the wall of the blood vessel to electrically connect the device to a power supply and controller.

Figure 1:
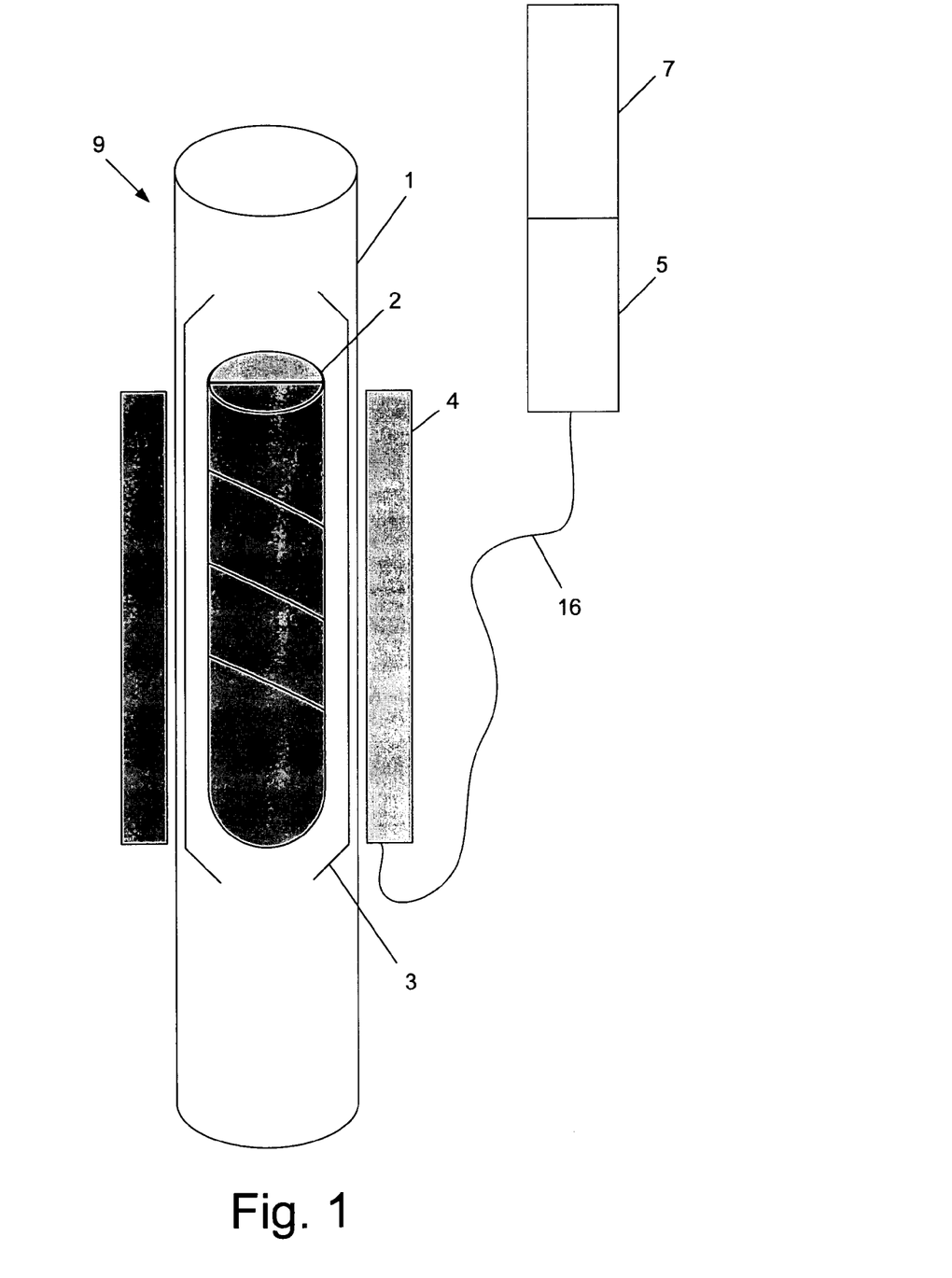
FIG. 1 schematically shows a longitudinal cross-sectional view of the permanent ventricular device (PVAD) of the invention implanted in a blood vessel.

The principal components of the PVAD 9 of the invention are shown schematically in FIG. 1. The device is a magnetic pump, comprising:

i) a passive core 2 (Pcore) fixed onto a chassis 3, either by means of a permanent connection or by a releasable connection using for example mechanical clips, and implanted inside a blood vessel 1;

ii) a stator 4 surrounding the outside of said blood vessel 1; and iii) an implantable unit comprising a power supply 5 and a controller 7 electrically connected to stator 4 by electrical wires 16 (note that for simplicity only one wire is shown to represent the many wires that make up the electrical circuit).

Figure 2:
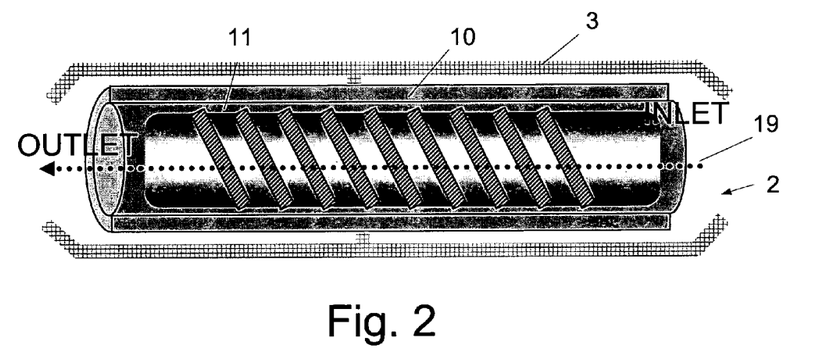
FIG. 2 schematically shows a longitudinal cross-sectional view of the rotor (Pcore), attached to a chassis.

Pcore 2 is shown schematically in FIG. 2. The Pcore 2 comprises a cylindrically shaped hollow body 10, which is designed to be implanted in to the blood vessel with its longitudinal axis 19 aligned in the direction of the blood flow. Pcore 2 further comprises a rotor 11, which is a cylinder with an Archimedes screw created on its outer surface, suspended co-axially within the hollow body 10 by means of magnetic bearings (see FIG. 3) situated at each end. The rotor 11 contains a permanent magnet 14 (see FIG. 3) embedded in it or is made of a permanently magnetized material. The permanent magnets of the Pcore are arranged such that their magnetic fields will interact with a synchronized varying magnetic field field created by the stator in such a way that the resulting magnetic force will cause rotor 11 to rotate. As the rotor 11 turns, the Archimedes screw pushes on the blood flowing through the hollow body 10, thereby increasing the blood flow rate.

Figure 3:
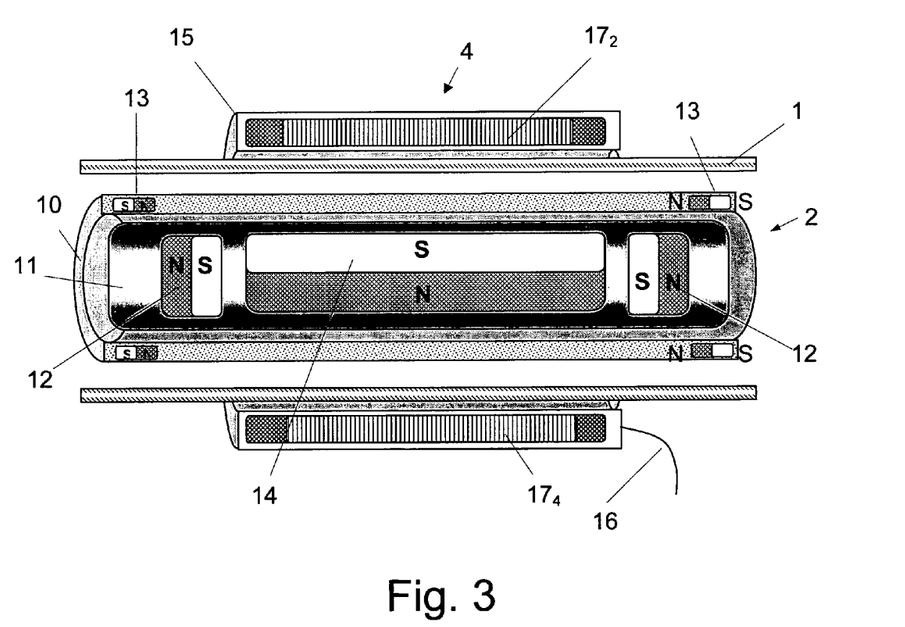
FIG. 3 schematically shows a longitudinal cross-section of the PVAD blood pump of the invention showing the arrangement of the permanent magnets and of the electromagnets.

FIG. 3 schematically illustrates an embodiment of an arrangement of permanent magnets utilized to achieve magnetic bearing support of the rotor. The rotor 11 is supported and held in place at each end by the sum of the forces exerted on it by the magnetic fields bar magnet 12 and ring magnet 13 at each end, arranged as shown in the figure. Magnet bearings suitable for use in the VAD of the invention are well known in the art and are described for example in U.S. Pat. No. 5,507, 629.

In one embodiment of the invention, Pcore 2 is attached to a chassis 3, in a way that it can be easily removed or replaced. In this case, the chassis 3 can be is preferably a stent that may be made of a memory retaining biocompatible material, such as nitinol, which allows the stent to be compressed before deployment to ease its insertion into a vessel, and thereafter self-expand intravascularly, pressing against the walls of the vessel to hold it in place. The Pcore 2 can be attached to the chassis 3 before implantation or after as described herein below. In another embodiment, the Pcore 2 can be placed inside the blood vessel and held in place by rings clamped around the artery on each side. In this case, Pcore 2 may have a niche in the hollow body 10 to enable proper tying. In this embodiment the chassis 3 is therefore not needed to anchor the Pcore.

Figure 4:
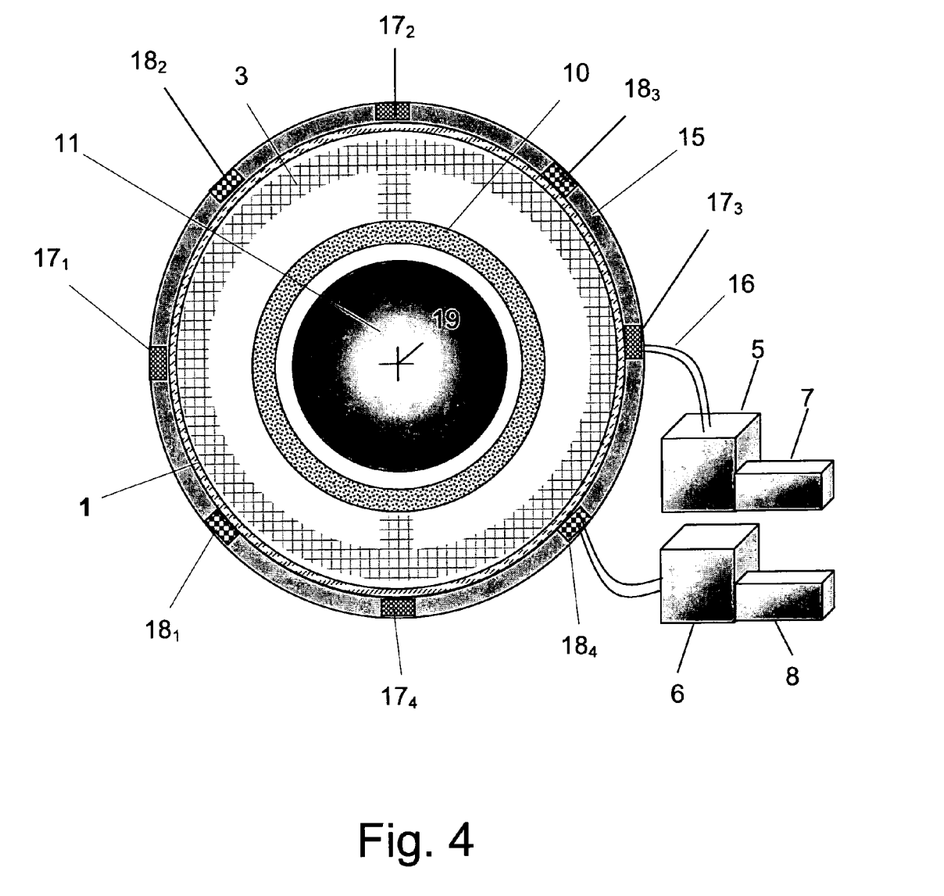
FIG. 4 schematically shows an axial cross-section of the PVAD blood pump showing the details of the pump stator.

The stator 4 is shown schematically in FIG. 3. It is located outside the blood vessel 1 and is capable of generating a time varying magnetic field which interacts with the magnetic field of the permanent magnet 14 of the rotor 11 to cause the rotor 11 to turn. In a preferred embodiment that is shown in FIG. 4, the stator 4 is composed of a flexible belt or bracelet 15 which comprises two sets 17 and 18 of four electromagnets each. In a preferred embodiment, the electromagnets are an elongated embodiment of planar bifilar coils (described for example in U.S. Pat. No. 512,340), which generate an electromagnetic field perpendicular to the plane of the coils. The electromagnets of each set are attached to belt 15, such that when belt 15 is attached to the outside of vessel 1, as it will be discussed herein below, the electromagnets are distributed symmetrically around the longitudinal axis 19 of rotor 11. Each electromagnet $17_1$-$17_4$ is electrically connected individually (most of the wires of the electrical connections are not shown in the figure) to power supply 5 and controller 7 so that each of them may be separately activated to cause the desired rotary movement of the rotor 11. Similarly, each electromagnet $18_1$-$18_4$ is connected to another power supply 6 and another controller 8. The electromagnets $17_1$-$17_4$ and their power supply 5 and controller 7 are used for normal operations and the second set of electromagnets $18_1$-$18_4$ is redundant and only used in case of a malfunction of the first set 17. As opposed to all devices known by the inventors, because the electromagnets, controller and the power supply are external to the blood vessel, it does not have to be cut or punctured in order to make the electrical connections.

The entire implantable device of the invention is made of biocompatible material such as titanium or plastic. The stator belt to which the coils of the electromagnets are attached can be made of Nitinol. Additionally all elements directly in contact with the blood, are coated with non-thrombogenic material, e.g. polyethylene glycol.

Figure 5:
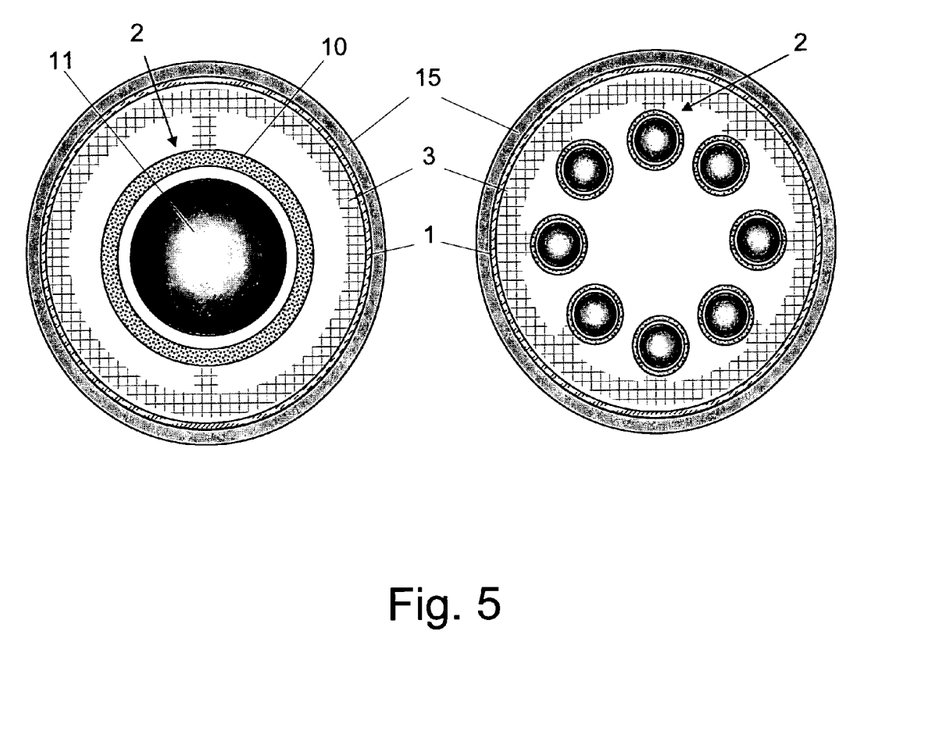
FIG. 5 schematically shows axial cross-sections of two embodiments of the PVAD.

The general characteristics of the PVAD of the present invention were described above, but in different embodiments several features, in particular the number of Pcores implanted in the blood vessel, may vary according to particular physiological conditions of the patient or his recovery status. FIG. 5 shows for example two embodiments of the present invention. In one embodiment, shown on the left of the figure, a single Pcore 2 having a length of about 4 cm and a diameter varying between 0.7 cm to 2 cm is shown inserted inside the blood vessel 1 and attached to a chassis 3, e.g. a stent. Rotation of the rotor in 11 inside Pcore body 10 is caused by the electromagnets of the stator that are attached to (or embedded in) belt 15 that is attached to the outer surface of blood vessel 1 surrounding the Pcore. The exact dimensions of the various components of the PVAD depend on several factors such as the location at which it is implanted and the implementation procedure used. In another embodiment, shown on the right in FIG. 5, several Pcores 2 are inserted in blood vessel 1, their number and their size depending on factors such as the medical condition of the patient and the diameter of the vessel into which the PVAD is implanted.

Figure 6A:
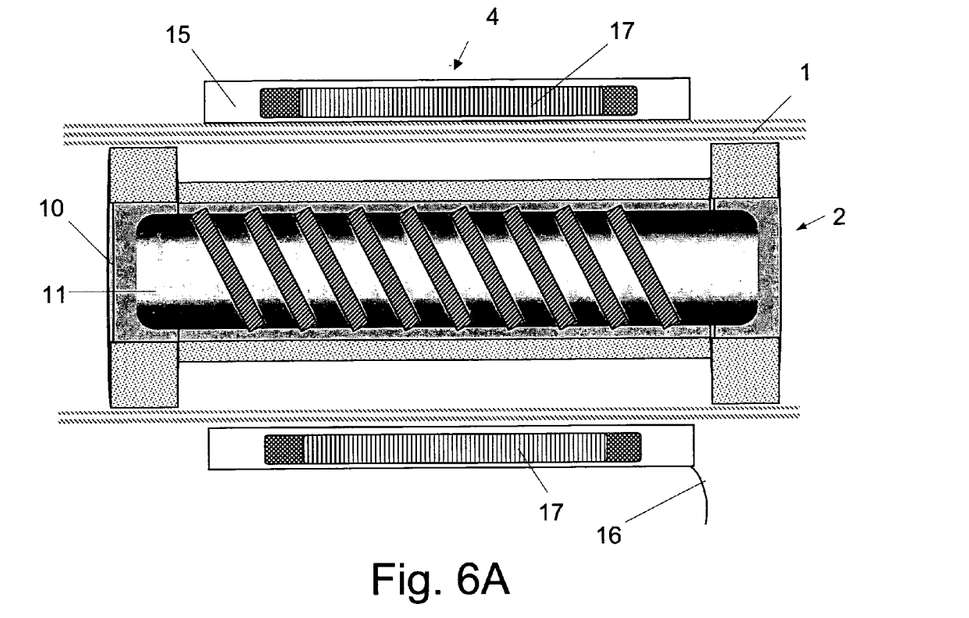
FIGS. 6A and 6B schematically show a method of installing the Pcore and stator in the cardiovascular system.
Figure 6B:
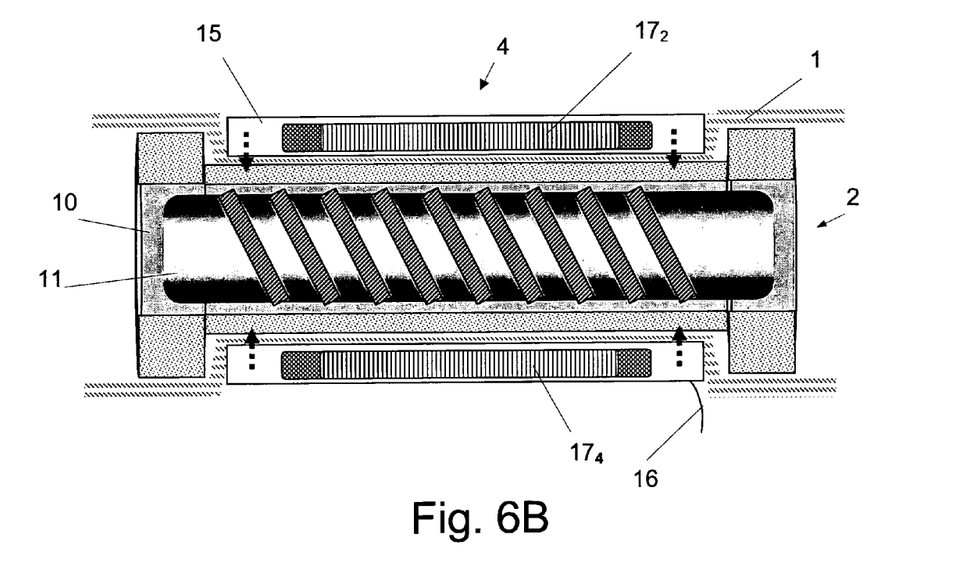

FIG. 6A and FIG. 6B schematically show another method of fixing the components of the PVAD at a location in the cardiovascular system. As shown in FIG. 6A, Pcore 2 is located inside blood vessel 1 at the desired location. In this case, no chassis is used. The stator 4 is then placed outside of and surrounding the walls of vessel 1 at the same location. The end sections of hollow body 10 of Pcore 2 have a larger diameter than the much longer middle section, thereby forming an annular indention at least as long as belt 15 that supports the stator. Belt 15 is now tightened around blood vessel 1, compressing the walls of blood vessel between the inner surface of belt 15 and the outer surface of the body 10 of Pcore 2 as shown in FIG. 6B. Care must be taken to find the proper balance between tightening belt 15 enough to anchor the Pcore and the stator in place without tightening it too much and causing necrosis of the tissue of the blood vessel.

The PVAD of the invention can be advantageously implanted at several locations in the cardiovascular system. Examples of such locations are the abdominal aorta, the ascending aorta, and descending aorta. The PVAD can be implanted in the abdominal aorta by open surgery or by a minimal invasive procedure using catheterization (for the Pcore) and laparoscopy (for the stator), which are common techniques used in most of the hospitals. It can be implanted in the ascending thoracic aorta by catheterization (for the Pcore) and thoracoscopia (for the stator). In preparation for surgery, computer tomography (CT) of the aorta is required to check the absence of operating contraindication. Outlines of the main steps typical non-limiting examples of medical procedures that can be used to implant the PVAD of the invention at these locations are given herein below.

A first illustrative procedure is for implanting the PVAD into the abdominal aorta. This is an open surgery procedure, which comprises the following steps:

i) Supine position; Trans-Eosophagial ECHO; CVP/Swan-Ganz catheter;
  ii) Exposing the abdominal aorta by midline laparotomy;
  iii) Introducing Systemic Heparin at a ratio of 1 mg/kg;
  iv) Clamping of the Aorta below the renal arteries and above the iliac arteries;
  v) Performing a 3 cm longitudinal cut in the aorta;
  vi) Inserting the Pcore and securing it to the aortic wall;
  vii) Suturing the aorta;
  viii) Placing the stator around the aorta;
  ix) Pulling out the electric command cable through the skin;
  x) Turning the PVAD on, gradually increasing the pump flow; and
  xi) Closing the skin.

Another procedure for introducing the PVAD into the lower-abdominal, renal-abdominal or descending thoracic aorta, is by introducing the Pcore by catheterization, comprising the following steps:

i) Positioning Supine; Trans-Eosophagial ECHO; CVP/Swan-Ganz catheter;
  ii) Opening the right groin;
  iii) Exposing the right femoral artery;
  iv) Introducing Systemic Heparin at a ratio of 1 mg/kg;
  v) Inserting a "working cuff" into the artery;
  vi) Inserting a J-Wire through the cuff;
  vii) Locating the wire under roentgen guidance to one of three possible locations:
    a) In the lower abdominal aorta;
    b) In the abdominal aorta, above the renal arteries just below the diaphragm;
    c) In the descending thoracic aorta;
  viii) Inserting the stent on the wire to its place;
  ix) Deploying the stent;
  x) Inserting the Pcore on the wire into the stent;
  xi) Anchoring the Pcore to the stent wall;
followed by the introduction of the stator by laparoscopy, as follows:
  xii) Positioning Trendelenburg;
  xiii) For the abdominal locations:
    a) Inserting a videoscopic trocar through the umbilicus;
    b) Inserting two working arms into the abdomen;
    c) Exposing the aorta through the retro-peritoneum;

xiv) For the thoracic location:
   a) Collapse of the left lung (right lung ventilation);
   b) Inserting a videoscopic trocar lateral to the nipple;
   c) Inserting two working arms into the left thorax;
   d) Exposing the aorta;
xv) Placing the stator around the Aorta; Roentgen guided position;
xvi) Pulling out the electric command cable through the skin;
xvii) Turning the VAD on, gradually increasing the pump flow;
xviii) Closing the skin;
xix) Pulling out the femoral cuff;
xx) Suturing the arteriotomy; and
xxi) Closing the skin of the groin.

A procedure for introducing the PVAD into the ascending thoracic aorta, is by introducing the Pcore by catheterization, comprising the following steps:
i) Positioning Supine. Trans-Eosophagial ECHO. CVP/Swan-Ganz catheter;
ii) Opening the right groin;
iii) Exposing the right femoral artery;
iv) Introducing Systemic Heparin at a ratio of 1 mg/kg;
v) Inserting a "working cuff" into the artery;
vi) Inserting a J-Wire through the cuff;
vii) Locating the wire under roentgen guidance in the ascending aorta;
viii) Inserting the stent on the wire to its place;
ix) Deploying the stent;
x) Inserting the Pcore on the wire into the stent;
xi) Anchoring the Pcore to the stent wall;
followed by the introduction of the stator by thoracoscopy, as follows:
xii) Ventilating left lung ventilation (Collapse right);
xiii) Inserting a videoscopic trocar through the right $4^{th}$ intercostals space;
xiv) Inserting two working arms into the right thorax;
xv) Exposing the ascending aorta through the pericard;
xvi) Placing the stator around the aorta;
xvii) Positioning guided by Roentgen.
xviii) Pulling out the electric command cable through the skin.
xix) Turning the VAD on, gradually increasing the pump flow;
xx) Closing the skin;
xxi) Pulling out the femoral cuff;
xxii) Suturing the arteriotomy; and
xxiii) Closing sub-cutane and skin of the groin.

Although several specific locations and procedures for implanting the PVAD of the present invention were described above, it is not the intention of the inventors to limit the invention to the locations or procedures described herein.

During the installation phase of the PVAD a ranging procedure (RP) is performed in order to adapt the PVAD to the specific installation parameters such as the number of Pcores used, the number of stator coils used, the structure of the aorta, the patient blood pressure and the distance between the PVAD to the heart. The ranging procedure is an experimental procedure to determine the optimal configuration for a given PVAD implanted at a given location. It is an iterative procedure that is done several times until optimal results are achieved.

The ranging procedure comprises the following steps:
i) assuming N coils in a symmetrical structure and using the controller to activate the coils in default configuration, by applying a pulse at the default power level for a specific time period while;
ii) opening a ranging window, i.e., stopping the signals to the coils and reading the signals coming back from each coil to the controller;
iii) closing the ranging window;
iv) determining the number of coils according to the number of returning signals; [This step is required since a standard stator belt is used containing a plurality of coils embedded within it. During the operation the belt is fitted to the specific patient's anatomy and the loose end of the belt is cut off and removed. This step automatically discloses the number of coils that remain in the belt after it has been fitted to the patient.]
v) determining the position of the coils according to the phase delay of each returning signal from each of the existing coils; [This step is necessary because the position of the coils varies due to different aorta anatomies. The controller learns during this stage the exact positions of the coils and determines the phase shift required for each coil.]
vi) determining the number of Pcores that are present; [This is done by measuring the impulse generated during the ranging procedure, which is determined from the amount of electrical energy applied to the stator for a known time interval. The rotational velocity of the Pcoils is measured by determining the frequency of the signals coming back from the stator coils. The total mass of the Pcores can be calculated from these values and therefore the number of Pcores operating is known. This step is essential in order to verify that the surgeon has actually installed the planned number of Pcores. Since if a Pcore fails the returning signal will be distorted and its frequency and duty cycle will change, this step can also be used during normal operation to verify that all the Pcores are functioning properly and to generate alarm in case of Pcore failure. This step can also be used during normal operation to sense changes in the condition of the patient's heart and to change the pumping flow accordingly. For example, if the heart starts recovering and pumping blood at a higher flow rate then the momentum delta measured in the ranging procedure decreases.]
vii) determining the voltage level required from the controller to maintain the correct RPM of the rotors; and
viii) generating an appropriate signal sequence, sending an electrical signal to each coils with the correct phase and voltage.

In pulsatile pumping mode, another step is performed in the ranging procedure to calibrate the phase of the pump pulses relative to the E.C.G. of the heart. This step consists of sending pulses from the controller to the pump, in different phase relative to the ECG and measuring the effect on the pump flow.

After the ranging procedure is completed the correct configuration is saved and performed; wherein by configuration is meant the correct voltage, timing, and firing sequence that must be applied to the coils of the stator in order to cause the rotor/s to rotate smoothly and provide the reuired assist to the blood flow.

The amount of help given to the heart by the PVAD can be adapted to the physiological state of the patient by varying the rotor speed and, in case of gradual recovery of the heart functions, the number of rotors installed in the chassis can be decreased. This can be done by replacing or removing the P-core when/if required. In cases in which the PVAD is installed as a "bridge to recovery", the Pcore can be removed from the aorta after the patient makes a full recovery. The removal of the Pcore is done by a catheterization procedure, identical to the insertion procedure while the stent and the stator will remain in the body.

Configuration commands can be given by the doctor to the controller by using RFID communication channel. In preferred embodiments of the PVAD of the invention, the heart rate and beat phase are continuously monitored by means of two needle electrodes permanently implanted in the subcutaneous tissue for ECG sensing. The controller adjusts the pump operation according to the ECG. For example in case where the heart rate changes the controller will adjust the phase shift to the modified cardiac cycle changing the output of the pump accordingly.

As said, the stator of the PVAD of the present invention contains two independent units to provide redundancy in case of technical failure. Each unit contains a set of electromagnet (17 and 18) located in the belt 15, a rechargeable power supply (5 and 6) and a controller (7 and 8). During the ranging procedure the controllers work in parallel to analyze the signals coming back from the sensors and from the coils. According to the results of this analysis it is decided which unit will be the primary one and which will act as the backup. To avoid disturbing the blood flow in case of Pcore malfunction, several Pcores are preferably used inside the aorta, or if alone, the diameter of said Pcore should not occupy the full aorta and hence leaves a place for natural flow.

Although embodiments of the invention have been described by way of illustration, it will be understood that the invention may be carried out with many variations, modifications, and adaptations, without exceeding the scope of the claims.

The invention claimed is:

1. A kit for a permanent ventricular assist device (PVAD) comprising:
   i) one or more passive cores ($P_{core}$);
   ii) a stator that is a flexible belt or bracelet comprising at least two independent sets of electromagnets;
   iii) a power supply; and
   iv) a controller unit; characterized in that said one or more $P_{cores}$ are configured to be implanted inside a blood vessel, and said stator is configured to be placed outside of said blood vessel surrounding said $P_{cores}$.

2. A kit according to claim 1, wherein the electromagnets are planar elongated bifilar coils.

3. A kit according to claim 1, wherein each set of electromagnets has its own power supply and controller.

4. A kit according to claim 3, wherein each electromagnet in a set is electrically connected separately to the power supply and the controller.

* * * * *